(12) United States Patent
Ichikawa et al.

(10) Patent No.: US 8,501,204 B2
(45) Date of Patent: Aug. 6, 2013

(54) METHOD FOR PRODUCING VESICLE, VESICLE OBTAINED BY THE PRODUCTION METHOD, AND W/O/W EMULSION FOR PRODUCING VESICLE

(75) Inventors: Sosaku Ichikawa, Ibaraki (JP); Takashi Kuroiwa, Tokyo (JP)

(73) Assignee: University of Tsukuba, Ibaraki (JP)

( * ) Notice: Subject to any disclaimer, the term of this patent is extended or adjusted under 35 U.S.C. 154(b) by 0 days.

(21) Appl. No.: 12/993,954

(22) PCT Filed: May 21, 2009

(86) PCT No.: PCT/JP2009/002242
§ 371 (c)(1),
(2), (4) Date: Feb. 25, 2011

(87) PCT Pub. No.: WO2009/142018
PCT Pub. Date: Nov. 26, 2009

(65) Prior Publication Data
US 2011/0150953 A1    Jun. 23, 2011

(30) Foreign Application Priority Data

May 23, 2008   (JP) .................................. 2008-135009

(51) Int. Cl.
    *A61K 8/02*   (2006.01)
(52) U.S. Cl.
    USPC ........................................................ 424/401
(58) Field of Classification Search
    None
    See application file for complete search history.

(56) References Cited

U.S. PATENT DOCUMENTS

| 4,687,661 A | 8/1987 | Kikuchi et al. |
| 6,106,858 A | 8/2000 | Ye et al. |
| 7,485,671 B2 * | 2/2009 | Qiu et al. ........................ 516/53 |

FOREIGN PATENT DOCUMENTS

| JP | 6-039274 A | 2/1994 |
| JP | 2003-001097 A | 1/2003 |
| JP | 2006239594 A | 9/2006 |
| JP | 2007-044692 A | 2/2007 |
| JP | 2007-284395 A | 11/2007 |
| JP | 2008-044962 A | 2/2008 |
| WO | WO 9925319 A1 * | 5/1999 |

OTHER PUBLICATIONS

Nii et al., Emulsification efficiency of water soluble and insoluble drugs in liposomes prepared by the microencapsulation vesicle method, Dec. 2004, International Journal of Pharmaceutics, 298, 198-205.*

(Continued)

*Primary Examiner* — Anand Desai
*Assistant Examiner* — Melissa Mercier
(74) *Attorney, Agent, or Firm* — Carrier Blackman & Associates, P.C.; William D. Blackman; Joseph P. Carrier (57) ABSTRACT

A vesicle is produced by: a step of producing a W/O emulsion from an aqueous solution containing a substance to be entrapped in a vesicle in a dissolved or suspended state and an organic solvent phase containing a lipid having emulsification capacity, which can constitute the vesicle; a step of producing a W/O/W emulsion from the W/O emulsion and an external water phase solution of a water-soluble emulsifier, which does not destroy a vesicle lipid membrane; and a step of removing the organic solvent phase from the W/O/W emulsion, so as to form a vesicle. This method simultaneously achieves a high entrapment yield of an active ingredient and the control of a particle diameter.

17 Claims, 5 Drawing Sheets

(56) References Cited

OTHER PUBLICATIONS

Ishii et al., "Preparation Conditions and Evaluation of the Stability of Lipid Vesicles (Liposomes) Using the Microencapsulation Technique", Journal of Dispersion Science and Technology, vol. 9, No. 1, 1988, Copyright 1988 by Marcel Dekker, Inc.

Szoka, Jr., et al., "Procedure for Preparation of Liposomes With Large Internal Aqueous Space and High Capture by Reverse-Phase Evaporation", Proceedings of the National Academy of Sciences of the United States of America, Sep. 1978, vol. 75, No. 9, pp. 4194-4198.

Nii et al., "Encapsulation Efficiency of Water-Soluble and Insoluble Drugs in Liposomes Prepared by the Microencapsulation Vesicle Method", International Journal of Pharmaceutics, vol. 298, No. 1, Jul. 14, 2005, pp. 198-205.

* cited by examiner

FIG.3 (a) W/O emulsion

FIG.3 (b) W/O/W emulsion

FIG.3 (c) Vesicle

METHOD FOR PRODUCING VESICLE, VESICLE OBTAINED BY THE PRODUCTION METHOD, AND W/O/W EMULSION FOR PRODUCING VESICLE

TECHNICAL FIELD

The present invention relates to: a method for producing a vesicle, and particularly to a method for producing a vesicle having a particle diameter between several tens of nm and several tens of μm, which comprises entrapping a desired water-soluble substance in the internal water phase portion in the vesicle (hereinafter referred to as "the internal water phase") by using a W/O/W emulsion produced from a W/O emulsion used as a starting substance, and a vesicle obtained by this production method; and a method for producing a W/O/W emulsion used in the production of the vesicle, and a W/O/W emulsion obtained by this production method.

BACKGROUND ART

A vesicle is also referred to as a liposome, and it is a small enclosed sac consisting of a lipid bimolecular membrane formed with amphiphilic lipid molecules and an internal water phase. Thus, it is anticipated that such a vesicle will be used for various purposes such as a model cell membrane, a DDS (drug delivery system) preparation, a food product capsule and a microreactor for research usage.

An example of the conventional method for producing a vesicle is a method comprising hydrating a thin lipid membrane formed on the surface of a solid. For example, a thin lipid membrane is formed on a glass substrate, and an aqueous solution that contains a substrate to be entrapped in a vesicle (hereinafter, referred to as an "entrapped substance") is then added thereto, followed by intensive shaking, so as to produce a vesicle. However, the particle diameters of vesicles obtained by this method are generally non-uniform, and the entrapment efficiency of entrapping a desired entrapped substance in the vesicle (hereinafter referred to as "entrapment yield") is extremely low. The term "entrapment yield" is used herein to mean "the ratio, expressed by percent by weight, of substances entrapped in a vesicle to those contained in the finally obtained vesicle suspension as a whole." Moreover, it has also been difficult for this method to obtain a relatively large vesicle having a particle diameter of a micrometer-scale.

In order to enhance the entrapment yield of a desired substance in a vesicle, an emulsion can be used. For example, a method called "reverse phase evaporation method" disclosed in Non Patent Literature 1 has been known. In this method, a water phase containing a desired entrapped substance is dispersed in a volatile organic solvent containing an amphiphilic lipid, such as chloroform or ether, to produce a W/O emulsion, and only the solvent is removed from the produced emulsion by evaporation, and an aqueous solution is then added to the residue, so as to form a vesicle having a particle diameter of approximately 200 to 1,000 nm.

Moreover, as disclosed in Non Patent Literature 2, there has also been proposed a method for producing a vesicle having a particle diameter of approximately several hundreds of nm, which comprises: dispersing a water phase containing a desired entrapped substance in a volatile organic solvent containing an amphiphilic lipid, such as chloroform or ether, to produce a W/O emulsion; then producing a W/O/W emulsion by a stirring emulsification method using water or a buffer as an external water phase solution; and then removing the organic solvent from the produced W/O/W emulsion. According to such a method, there is a case in which a relatively high entrapment yield, such as an entrapment yield of 30% to 60%, may be achieved, and thus, this method is currently used as a method effective for entrapping a substance in a vesicle. Furthermore, Non Patent Literature 3 includes a report regarding the entrapment yield of a hydrophilic substance.

Patent Literature 1 by the present inventors discloses an effective method for producing a vesicle comprising: producing a W/O emulsion from a water phase containing an entrapped substance and an oil phase containing an emulsifier; freezing only an internal water phase; and then substituting the aforementioned emulsifier with a lipid, wherein this method differs from the method of the present invention.

Prior Art

Patented Documents

Patent Literature 1: Japanese Patent No. 4009733

Non-Patent Documents

Non Patent Literature 1: Szoka et al.: Proc. Natl. Acad. Sci. USA, vol. 75, No. 9, 4194-4198, 1978.

Non Patent Literature 2: Ishii et al.: J. Dispersion Sci. Technol., vol. 9, No. 1, 1-15, 1988.

Non Patent Literature 3: Nii and Ishii. Int. J. Pharmaceutics, vol. 298, 198-195, 2005

DISCLOSURE OF THE INVENTION

Object of the Invention

In the methods disclosed in Non Patent Literature 1 and Non Patent Literature 2, chloroform, benzene and the like, which are harmful to human bodies, are used as volatile solvents, and the use of vesicles produced by these methods for food products is therefore limited. Therefore, it would be advantageous to provide an improved method using an organic solvent which is free of chloroform. Moreover, even applying these known methods, it is still difficult to stably achieve high entrapment yields, and thus, approximately 40% to 70% of entrapped substances are not entrapped in vesicles, but they are present in a state in which they are dissolved in the external water phases of such vesicles. Furthermore, in the two methods, it is difficult to control the size of the obtained vesicle.

Accordingly, it has been desired to develop a method for producing a vesicle, which simultaneously achieves a high entrapment yield and the control of a particle diameter. Under such circumstances, the present invention provides a method for producing a vesicle, which can simultaneously achieve a high entrapment yield and the control of a particle diameter, as with the above described method for producing a vesicle of Patent Literature 1.

Means to Solve the Problem

In order to solve the aforementioned problems, the method for producing a vesicle of the present invention comprises the following steps (1) to (3):

(1) a step of producing a W/O emulsion from an aqueous solution containing a substance to be entrapped in a vesicle in a dissolved or suspended state and an organic solvent phase containing a lipid having emulsification capacity, which can constitute the vesicle;

(2) a step of producing a W/O/W emulsion from the W/O emulsion and an external water phase solution of a water-soluble emulsifier, which does not destroy a vesicle lipid membrane; and (3) a step of removing the organic solvent phase from the W/O/W emulsion, so as to form a vesicle.

Although the above described substance to be entrapped is a water-soluble substance, a vesicle with a high entrapment yield can be produced according to the method of the present invention. As such a substance to be entrapped, at least one substance selected from among substances used for pharmaceutical preparations, food products, supplements and cosmetic products may be adopted.

On the other hand, a hydrophobic substance may be contained in the above described organic solvent phase. As such a hydrophobic substance, at least one substance may be selected from among substances used for pharmaceutical preparations, food products, supplements and cosmetic products.

The above described W/O/W emulsion is preferably emulsified by a microchannel emulsification method, in order not to give an excessive share to a substance to be treated.

In addition, the method for producing a W/O/W emulsion used in the production of a vesicle according to the present invention comprises the following steps (1) and (2):

(1) a step of producing a W/O emulsion from an aqueous solution containing a substance to be entrapped in a vesicle in a dissolved or suspended state and an organic solvent phase containing a lipid having emulsification capacity, which can constitute the vesicle; and (2) a step of producing a W/O/W emulsion from the W/O emulsion and an external water phase solution of a water-soluble emulsifier, which does not destroy a vesicle lipid membrane.

In the method for producing a vesicle according to the present invention, a W/O emulsion is produced from an aqueous solution containing a substance to be entrapped in a vesicle in a dissolved or suspended state, and an organic solvent phase, which contains a lipid species (for example, a phospholipid such as phosphatidyl choline) functioning as an emulsifier and having emulsification capacity, which can constitute the vesicle, and then, the W/O emulsion is dispersed in an aqueous solution containing an emulsifier, which does not destroy a vesicle lipid membrane, to produce a W/O/W emulsion, and thereafter, the organic solvent phase is removed from the W/O/W emulsion. By this method, a thin lipid membrane is formed along the circumference of the water droplet in the W/O/W emulsion containing a substance to be entrapped in a vesicle, so that a vesicle containing a desired entrapped substance can be formed.

The type of a solvent used as an organic solvent phase of the above described W/O emulsion and W/O/W emulsion is not particularly limited, as long as it is a volatile organic solvent, which is capable of dissolving a vesicle-constituting lipid and is non-miscible with water. In addition, the type of an emulsifier contained in the external water phase solution of the above described W/O/W emulsion is not particularly limited, as long as it does not prevent the formation of a thin lipid membrane after the removal of the organic solvent.

In the conventionally proposed method for producing a vesicle using a W/O/W emulsion, water or a buffer has been used as an external water phase solution of the W/O/W emulsion, and the W/O/W emulsion has been produced by a stirring emulsification method. In the present invention, however, a hydrophilic emulsifier capable of stabilizing emulsion liquid droplets is added into such an external water phase solution, and an emulsification method having an extremely small mechanical shearing force during the emulsification operation, such as a microchannel emulsification method, is adopted, so that the leakage of the entrapped substance from the W/O/W emulsion and the disintegration of the thin lipid membrane of a vesicle obtained by the subsequent step can be prevented, thereby achieving the improvement of an entrapment yield.

Effect of the Invention

According to the present invention, it is possible to produce a vesicle, which achieves a high entrapment yield with respect to a desired substance, while controlling desired physical properties, such as the particle diameter of a vesicle. In addition, it is also possible to produce a vesicle by the combined use of highly safe chemical substances, which can be used as materials for pharmaceutical preparations or food products, and further, it is also possible to produce a vesicle having a sufficient strength (shape-maintaining ability) necessary for a model cell membrane, a DDS preparation and a microreactor for research usage. Specific effects of the present invention are as follows, for example.

(1) It is possible to entrap a substance in a vesicle at a high entrapment yield. Moreover, the type of the entrapped substance is not particularly limited, as long as it is a substance that can be dissolved or dispersed in the dispersed water phase of a W/O emulsion, and such an entrapped substance can be entrapped in a vesicle. Accordingly, the vesicle produced by the present invention can be used as a carrier of hydrophilic and hydrophobic drugs for a DDS preparation, or it can also be used as a microreactor for performing reactions regarding a useful gene or protein in a vesicle in the screening of a useful ingredient.

(2) According to the production method of the present invention, there can be stably provided a vesicle having a desired mean particle diameter within the range between approximately 0.05 µm and 100 µm, which has been difficult to be produced by the conventional method for producing a vesicle. The term "mean particle diameter" is used herein to mean a particle diameter calculated as a geometric mean based on a number standard in the number distribution of vesicle particle diameters.

(3) By selecting an amphiphilic lipid species dissolved in the organic solvent phases of W/O and W/O/W emulsions, vesicles having various lipid compositions can be relatively easily produced.

As stated above, since highly safe raw materials usable in all food products can be used as raw materials in the production process, the obtained vesicle can be anticipated to have high safety.

Accordingly, in addition to the conventionally intended use as a carrier of drugs for a DDS preparation and the like, the vesicle of the present invention can also be preferably used as a carrier of food product-related ingredients and cosmetic product-related ingredients, which could not be applied by existing methods. For example, the present vesicle can be used as a capsule material for food products containing various types of vitamins or as a carrier capable of promoting or suppressing the absorption of nutritional ingredients in the reinforcement of the functions of food products, or it can be applied to functional skin lotions, which utilize vesicles containing moisturizing ingredients and whitening ingredients.

BRIEF DISCRIPTION OF THE DRAWINGS

[FIG. 1]

[FIG. 2] FIG. 2(a) is a conceptual view showing an example of an apparatus for producing a vesicle, and (b) is a view showing an example of the configuration of flow.

[FIG. 3] FIG. 3(a) is a microphotograph of the W/O emulsion of Example 1, (b) is a microphotograph of the W/O/W emulsion of Example 1, and (c) is a microphotograph of the vesicle of Example 1.

[FIG. 4] FIG. 4(a) is a view showing the particle diameter distribution of the vesicle of Example 1, and (b) is a view showing the particle diameter distribution of the vesicle of Example 2.

[FIG. 5]

[FIG. 6]

[FIG. 7]

[FIG. 8]

EMBODIMENTS OF THE INVENTION

The vesicle of the present invention contains various substances such as a water-soluble substance, a solid particle or a cell, in the internal water phase thereof, and its mean particle diameter is between several tens of nm and several tens of μm. In addition, the vesicle of the present invention includes a particle having a microcapsule structure, in which a layer consisting of lipid molecules capable of constituting the vesicle (wherein the layer may not necessarily take a molecular membrane structure) is used as a wall material, as well as a vesicle constituted with the above described lipid bimolecular membrane.

The lipid species that constitutes the vesicle of the present invention (hereinafter referred to as a "vesicle-constituting lipid") may be a lipid having emulsification capacity, which can form the vesicle, namely, an amphiphilic lipid. Examples of such a lipid species include: phospholipids and sphingolipids such as phosphatidyl choline, phosphatidyl glycerol, phosphatidyl inositol, phosphatidic acid and phosphatidyl serine; emulsifiers used for food products, such as sorbitan fatty acid ester and polyglycerine fatty acid ester; and fatty acids such as oleic acid.

Moreover, other ingredients such as a lipid acting as a stabilizer for stabilizing an emulsion or a vesicle may also be comprised in the vesicle within the range that does not impair the advantages of the present invention. Examples of such other ingredients include: sterols such as cholesterol and ergosterol; charged lipids such as stearylamine; and long chain fatty acids such as oleic acid, stearic acid and palmitic acid. Furthermore, peptides and carbohydrates, which can interact with a lipid bimolecular membrane, may also be used in combination.

Figure 1:
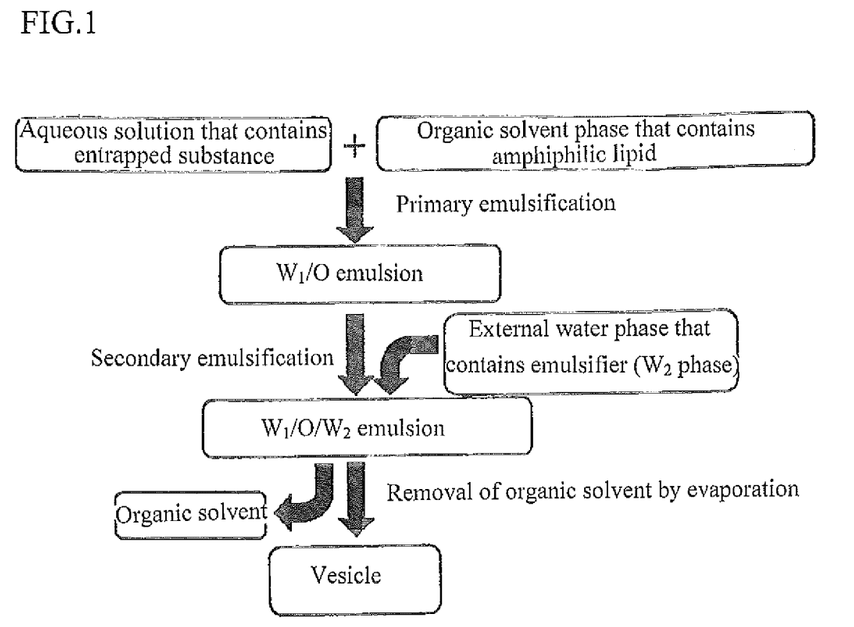
FIG. 1 shows a flow chart showing an example of the method for producing a vesicle of the present invention.

FIG. 1 is a flow chart showing an example of the method for producing a vesicle of the present invention. As shown in the figure, a water phase solution containing an entrapped substance is mixed with an organic solvent phase containing an amphiphilic lipid, and a $W_1/O$ emulsion having a desired liquid droplet diameter is produced using an existing emulsifying apparatus (hereinafter, the present step is referred to as a "primary emulsification step"). As a water phase of the $W_1/O$ emulsion, pure water, a solution of salts or sugars, or a buffer containing these substances can be used, and the entrapped substance can be dissolved or dispersed in such a water phase and can be then used. As an organic solvent phase of the $W_1/O$ emulsion, organic solvents that are non-miscible with water, such as n-hexane (hereinafter simply referred to as hexane), can be used. Preferably, the organic solvent phase used is free of chloroform.

The above-mentioned existing emulsifiable amphiphilic lipid has previously been mixed into such an organic solvent phase. An emulsifying apparatus used for the $W_1/O$ emulsion may be appropriately selected from existing emulsifying apparatuses such as an ultrasonic emulsifying apparatus, a stirring emulsifying apparatus, a membrane emulsifying apparatus, a microchannel emulsifying apparatus and a high pressure homogenizer, depending on the liquid droplet diameter of an emulsion to be produced.

In the subsequent step, the above described $W_1/O$ emulsion is used as a dispersion phase, and an external water phase solution containing a water-soluble emulsifier that does not destroy a vesicle lipid membrane is used as a continuous phase, so as to produce a $W_1/O/W_2$ emulsion (hereinafter, the present step is referred to as a "secondary emulsification step"). Various types of existing emulsification methods can be applied to produce the $W_1/O/W_2$ emulsion. Among others, a microchannel emulsification method, which does not need a large mechanical shearing force for an emulsification treatment, is most effective because this method suppresses the disintegration of liquid droplets and the leakage of entrapped substances from the liquid droplets during the emulsification operation.

The composition of the above described external water phase may be either identical to or different from the composition of the above described internal phase containing the entrapped substances, and the composition of the external water phase is not particularly limited, as long as it does not prevent the formation of a vesicle in the subsequent step. However, in order to improve an entrapment yield, it is desired to use an external water phase solution having an osmotic pressure identical to or close to that of the water phase solution containing the entrapped substances. As a hydrophilic emulsifier mixed into the external water phase solution, a hydrophilic emulsifier, which does not prevent the formation of a vesicle lipid membrane in the subsequent step, may be used, and for example, a protein emulsifier such as casein sodium is effectively used.

When a $W_1/O/W_2$ emulsion is produced by the above described microchannel emulsification method, there is used a microchannel emulsifying apparatus module, which is composed of a microchannel substrate (a) made of silicon and a glass plate (b) that covers the upper portion of the substrate. The outlet side of a gloved-type microchannel formed from the above described (a) and (b), or the outlet side of a through-hole type microchannel processed on the microchannel substrate (a) is filled with the above described external water phase solution, and the above described $W_1/O$ emulsion containing the entrapped substances is press-fitted from the inlet side of the microchannel, so that the $W_1/O/W_2$ emulsion can be produced. As microchannel substrates, substrates having various forms, such as a dead-end type, a cross-flow type and a through-hole type, can be used.

Subsequently, the produced $W_1/O/W_2$ emulsion is recovered, and it is then transferred into an open vessel, followed by leaving it at rest, so that the organic solvent phase is removed from the $W_1/O/W_2$ emulsion by evaporation. Thereby, a thin lipid membrane is formed from the amphiphilic lipid, which has been dissolved in the organic solvent phase, along the circumference of the internal water phase droplet containing the entrapped substance, so that a vesicle can be obtained.

Figure 2:
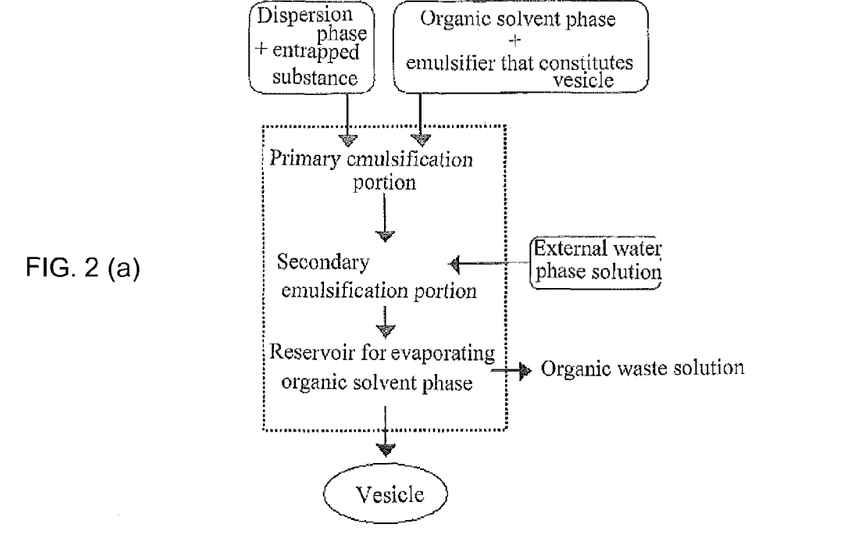

By integrating the above described steps, there can be produced an apparatus capable of semi-automatically producing a vesicle only by introducing various types of ingredients into the apparatus. FIG. 2(a) is a conceptual view showing an example of an apparatus for producing a vesicle, and (b) is a view showing an example of the configuration of the flow.

It has been difficult for the prior art techniques to efficiently entrapping a substance in a vesicle having any given particle diameter from several tens of nm to several tens of µm, and at the same time to produce a large number of similar vesicles. According to the production method and apparatus of the present invention, large quantities of vesicles each containing desired substances at a high entrapment yield of approximately several tens of percent can be obtained at one time, without determining complicated conditions such as heating, cooling and decompression.

Hereinafter, specific examples will be described. These examples are not intended to limit the scope of the present invention. The symbol "%" is used in the examples to indicate "percent by weight concentration."

EXAMPLE 1

(Amphiphilic Lipid, which Constitutes Vesicle)

A mixture consisting of yolk-derived phosphatidyl choline (hereinafter referred to as "PC") as a neutral phospholipid, cholesterol (hereinafter referred to as "Chol") as a representative cholesterol, and oleic acid (hereinafter referred to as "OA") as long chain fatty acid, was used as an amphiphilic lipid, which constituted a vesicle.

(Production of W/O Emulsion by Primary Emulsification Step)

Hexane, which contained 3% PC, and Chol and OA in amounts equimolar to the PC, was used as an organic solvent phase, and a Tris-HCl buffer (pH 9; 50 mmol/L) was used as a water dispersion phase used as an internal water phase, and emulsification was carried out by an ultrasonic treatment. Specifically, the organic solvent phase serving as a continuous phase was mixed with the dispersion phase so that the volume fraction of the dispersion phase became 25%, and thereafter, the mixture was gently shaken in an ultrasonic tank (output: 300 W) for 5 minutes, so as to produce a W/O emulsion. It is to be noted that calcein used as an entrapped substance had been dissolved in the water dispersion phase to a concentration of 0.4 mmol/L.

Figure 3:
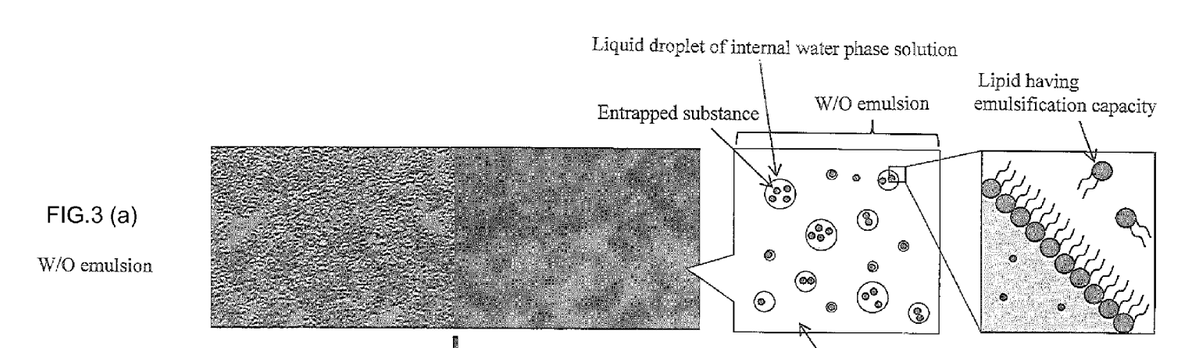

The mean particle diameter of water droplets contained in the produced W/O emulsion was approximately 2 µm (measured with a laser diffraction particle size analyzer), and it was confirmed by a microscopic image that calcein used as an entrapped substance was contained in the water droplets. This microscopic image is shown in FIG. 3(a).

(Production of W/O/W Emulsion by Secondary Emulsification Step)

Subsequently, using the above described W/O emulsion as a dispersion phase, a W/O/W emulsion was produced by a microchannel emulsification method. For the production of such a W/O/W emulsion, a dead-end type microchannel emulsifying apparatus module for experimental use was used. The microchannel substrate of this module was made of silicon, and the terrace length, channel depth and channel width of the microchannel substrate were approximately 60 µm, approximately 11 µm and approximately 16 µm, respectively.

A glass plate was press-fitted to the above described microchannel substrate to form a channel, and the outlet side of this channel was filled with a Tris-HCl buffer (pH 9; 50 mmol/L) containing 3% casein sodium, which was used as an external water phase solution, and the above described W/O emulsion was then supplied from the inlet side of the channel, so as to produce a W/O/W emulsion.

As a result of the observation of the microscopic image shown in FIG. 3(b), the mean liquid droplet diameter of the produced W/O/W emulsion was found to be approximately 30 µm, and it was confirmed that water droplets, each of which had almost the same size as the water droplet of the W/O emulsion and contained calcein as an entrapped substance, were contained in the liquid droplets. Hereinafter, water droplets contained in the W/O/W emulsion are referred to as "internal water phase droplets."

(Production of Vesicle by Removal of Organic Solvent Phase)

Thereafter, the above described W/O/W emulsion was transferred into an open glass vessel with no lid, and it was then left at rest at a room temperature for approximately 20 hours. From the fluorescent microscopic image shown in FIG. 3(c), it was confirmed that hexane contained in the W/O/W emulsion disappeared as a result of the aforementioned operation, that a suspension of fine vesicle particles could be obtained, and that calcein was contained in these particles.

Figure 4:
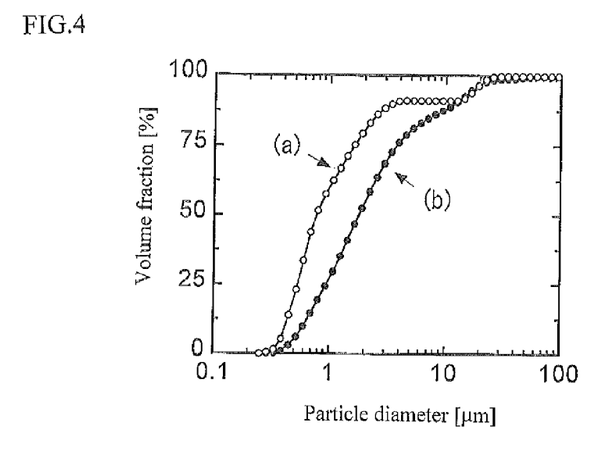
Figure 7:
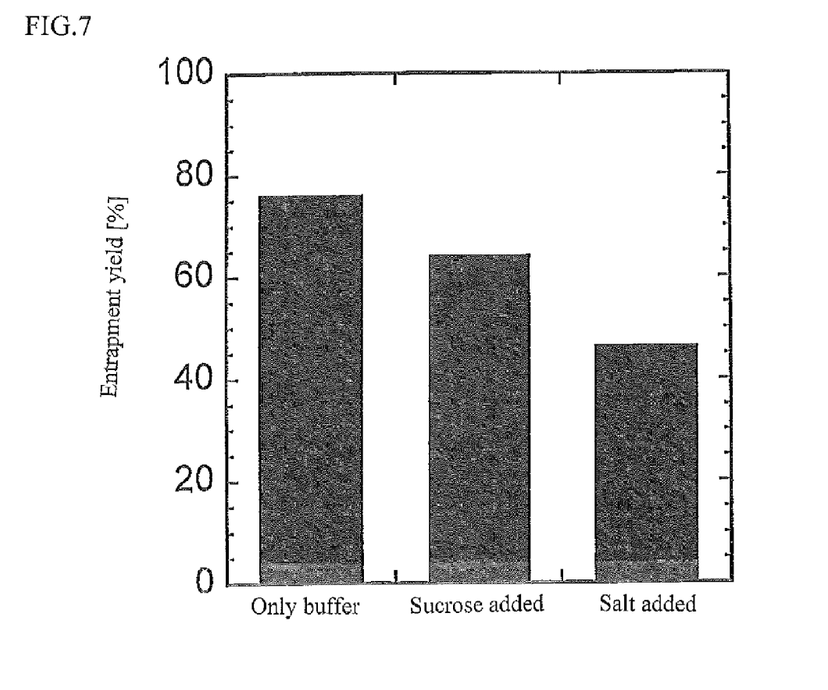
FIG. 7 is a graph showing the entrapment yield of a hydrophilic substance in a vesicle, in each case of only a buffer, the addition of sucrose, and the addition of salt.

Moreover, from the curve (a) of the graph shown in FIG. 4, which was made with a laser diffraction particle size analyzer, it was revealed that the mean particle diameter of this vesicle was approximately 1 µm. Furthermore, the entrapment yield of calcein, which was measured based on the method of Oku et al. (Oku et al.: Biochim. Biophys. Acta, vol. 691, 332-340, 1982), was approximately 76%, as shown in the graph of FIG. 7.

EXAMPLE 2

In the primary emulsification step, a rotor/stator type homogenizer was used instead of the ultrasonic tank of Example 1, so as to produce a W/O emulsion having a different mean water droplet diameter. Using this W/O emulsion, the particle size of the finally obtained vesicle, it was attempted to change.

(Production of W/O Emulsion by Primary Emulsification Step)

Figure 5:
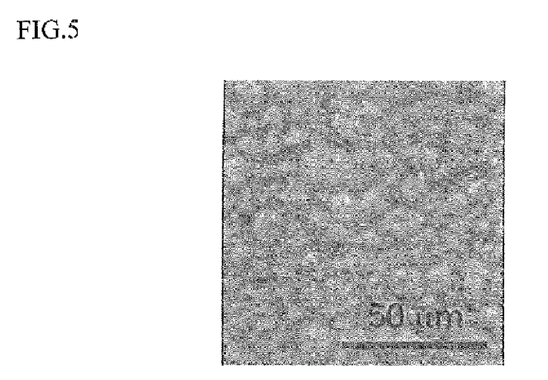
FIG. 5 is a microphotograph of the W/O emulsion of Example 2.

Using the same continuous phase and dispersion phase as those used in Example 1, the continuous phase was mixed with the dispersion phase so that the volume fraction of the dispersion phase became 25%, and thereafter, the mixture was emulsified using a rotor/stator type homogenizer at a rotation rate of 18,000 rpm for 5 minutes, so as to produce a W/O emulsion. FIG. 5 shows a microscopic image of the obtained W/O emulsion. As a result of a measurement using a laser diffraction particle size analyzer, the mean particle diameter of water droplets contained in this W/O emulsion was found to be approximately 5 µm.

(Production of W/O/W Emulsion by Secondary Emulsification Step)

Figure 6:
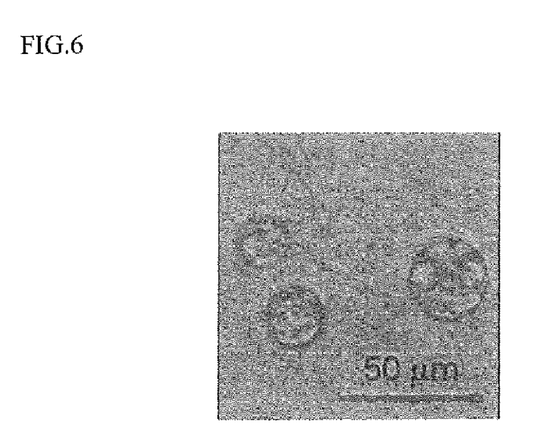
FIG. 6 is a microphotograph of the W/O/W emulsion of Example 2.

Using the above described W/O emulsion, a W/O/W emulsion was produced according to the same apparatuses and procedures as those used in Example 1. From the microscopic image shown in FIG. 6, it was found that the mean liquid droplet diameter of this W/O/W emulsion was approximately 22 µm, and that the W/O/W emulsion contained internal water phase droplets having almost the same size of the water droplets of the above described W/O emulsion.

(Production of Vesicle by Removal of Organic Solvent Phase)

A vesicle was produced from the above described W/O/W emulsion by the same procedures as those applied in Example 1. As shown in the curve (b) of FIG. 4, the mean particle diameter of this vesicle measured with a laser diffraction particle size analyzer was approximately 2 µm. That is to say, a W/O emulsion, the mean particle water droplet diameter of which was large, was produced by the above described primary emulsification step, and the produced W/O emulsion was used in the subsequent secondary emulsification step and in a further subsequent production of a vesicle by the removal of the organic solvent phase, so that a larger vesicle could be obtained.

EXAMPLE 3

A vesicle was produced by the same procedures as those applied in Example 1, except that a Tris-HCl buffer (50 mmol/L; pH 9) containing 500 mmol/L sucrose or sodium chloride was used instead of the dispersion phase of the primary emulsification step and the external water phase solution of the secondary emulsification step in Example 1.

The mean particle diameters of the obtained vesicles were both approximately 1 μm. As shown in the graph of FIG. 7, the entrapment yields of calcein measured in the same manner as that of Example 1 were approximately 64% and approximately 46% in the case of the addition of sucrose and in the case of the addition of sodium chloride, respectively.

Figure 8:
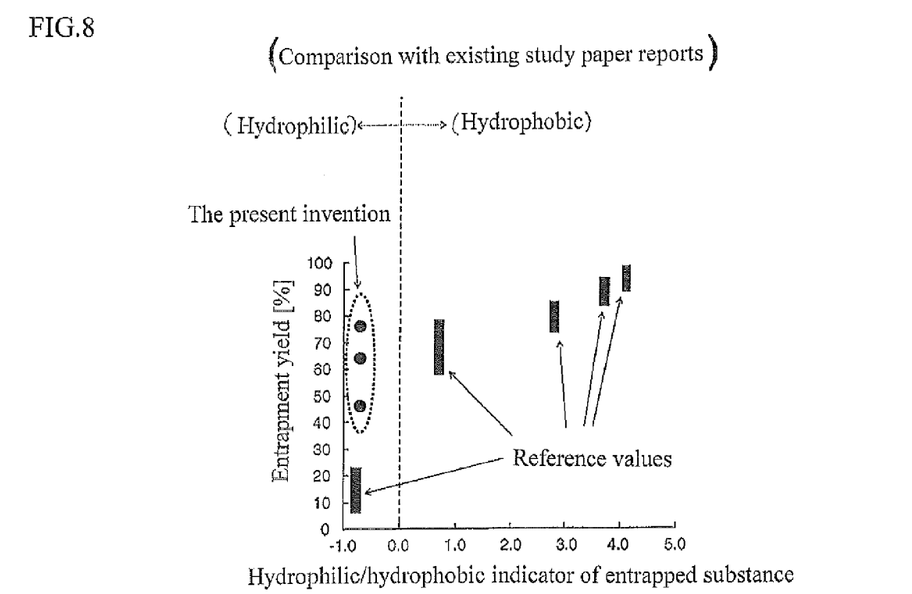
FIG. 8 is a graph in which the existing methods are compared with the method of the present invention in terms of the entrapment yield of a hydrophilic substance.

That is, as shown in the graph of FIG. 8 (which was produced based on Non Patent Literature 3), it was found that, even under difficult conditions in which an aqueous solution containing a highly hydrophilic entrapped substance such as a sugar or salt was used, vesicles were produced at entrapment yields higher than or equivalent to those obtained by the existing methods as described in Non Patent Literatures 1 and 2.

INDUSTRIAL APPLICABILITY

According to the production method of the present invention, there can be produced a vesicle, which efficiently entraps a water-soluble substance, which has been difficult to achieve by existing methods for producing a vesicle. A vesicle has already been used as a carrier of hydrophobic drugs in the industrial field, but a vesicle produced by the present invention can be applied as a carrier of water-soluble drugs in a drug delivery system, and thus, it is anticipated that the present vesicle can be effectively used in the field of pharmaceutical preparations.

For example, if a hydrophilic drug is dissolved in a dispersion phase and a hydrophobic drug is dissolved in an organic solvent phase in the primary emulsification step, and if a vesicle is then produced by the procedures described in the above Examples, then simultaneously, the hydrophilic drug can be retained in the internal water phase of the vesicle and the hydrophobic drug can be retained in the lipid membrane of the vesicle. Thereby, it is anticipated that the present production method can be applied to new pharmaceutical products, in which two hydrophilic and hydrophobic drugs are allowed to simultaneously act on affected area, wherein it has been previously difficult to simultaneously deliver the two drugs to the affected area.

Furthermore, differing from existing production methods, since a vesicle can be produced using only ingredients available to the food industry in the present invention, the vesicle produced by the present invention can be used for food products, supplements, cosmetic products, pharmaceutical products for use in oral administration, and the like. For instance, if an enzyme supporting the digestion of food products is entrapped in a vesicle and the vesicle is then added to a food product containing many ingredients decomposed by the above described enzyme, after the ingestion of the food product, the vesicle is disintegrated in a body to release the enzyme, and as a result, it can be anticipated that the effect of promoting the digestion of food ingredients, etc. can be obtained.

Still further, also in the field of cosmetic products, since both a hydrophobic whitening ingredient and a hydrophilic moisturizing ingredient can be simultaneously entrapped in the vesicle, the vesicle can be anticipated to be used for skin lotions having new functions, etc.

The invention claimed is:

1. A method for producing a vesicle, which comprises the following steps (1) to (3):
   (1) a step of producing a W/O emulsion from an aqueous solution containing a substance to be entrapped in a vesicle in a dissolved or suspended state, and an organic solvent phase containing a vesicle-constituting lipid having emulsification capacity, which can constitute the vesicle, and a stabilizer lipid selected from the group consisting of sterols, charged lipids, long chain fatty acids, and mixtures thereof;
   (2) a step of producing a W/O/W emulsion from the W/O emulsion and an external water phase solution containing a protein emulsifier comprising casein sodium as a water-soluble emulsifier, which does not destroy a vesicle lipid membrane; and
   (3) a step of removing the organic solvent phase from the W/O/W emulsion, so as to form a vesicle.

2. The method for producing a vesicle according to claim 1, wherein the substance to be entrapped is a water-soluble substance.

3. The method for producing a vesicle according to claim 1, wherein the substance to be entrapped is at least one substance selected from among substances used for pharmaceutical preparations, food products, supplements and cosmetic products.

4. The method for producing a vesicle according to claim 1, which comprises mixing a hydrophobic substance into the organic solvent phase.

5. The method for producing a vesicle according to claim 4, wherein the hydrophobic substance is at least one substance selected from among substances used for pharmaceutical preparations, food products, supplements and cosmetic products.

6. The method for producing a vesicle according to claim 1, wherein the W/O/W emulsion is emulsified by a microchannel emulsification method.

7. A vesicle produced by the method for producing a vesicle according to claim 1.

8. A method for producing a W/O/W emulsion used in the production of a vesicle, which comprises the following steps (1) and (2):
   (1) a step of producing a W/O emulsion from an aqueous solution containing a substance to be entrapped in a vesicle in a dissolved or suspended state and an organic solvent phase containing a vesicle-constituting lipid having emulsification capacity, which can constitute the vesicle, and a stabilizer lipid selected from the group consisting of sterols, charged lipids, long chain fatty acids, and mixtures thereof; and
   (2) a step of producing a W/O/W emulsion from the W/O emulsion and an external water phase solution containing a protein emulsifier comprising casein sodium as a water-soluble emulsifier, which does not destroy a vesicle lipid membrane.

9. A W/O/W emulsion produced by the method for producing a W/O/W emulsion according to claim 8.

10. The method for producing a vesicle according to claim 2, wherein the substance to be entrapped is at least one substance selected from among substances used for pharmaceutical preparations, food products, supplements and cosmetic products.

11. A vesicle produced by the method for producing a vesicle according to claim 2.

12. A method for producing a vesicle, which comprises the following steps (1) to (3):
   (1) a step of producing a W/O emulsion from an aqueous solution containing a substance to be entrapped in a vesicle in a dissolved or suspended state and an organic solvent phase containing hexane, a vesicle-constituting lipid having emulsification capacity, and a stabilizer lipid selected from the group consisting of sterols, charged lipids, long chain fatty acids, and mixtures thereof;
   (2) a step of producing a W/O/W emulsion by a microchannel emulsification method using a microchannel apparatus, from the W/O emulsion and an external water phase solution containing a protein emulsifier comprising casein sodium as a water-soluble emulsifier which does not destroy a vesicle lipid membrane; and
   (3) a step of removing the organic solvent phase from the W/O/W emulsion, so as to form a vesicle.

13. The method for producing a vesicle according to claim 12, wherein the substance to be entrapped is a water-soluble substance.

14. The method for producing a vesicle according to claim 12, wherein the substance to be entrapped is at least one substance selected from among substances used for pharmaceutical preparations, food products, supplements and cosmetic products.

15. The method for producing a vesicle according to claim 12, which comprises mixing a hydrophobic substance into the organic solvent phase.

16. The method for producing a vesicle according to claim 15, wherein the hydrophobic substance is at least one substance selected from among substances used for pharmaceutical preparations, food products, supplements and cosmetic products.

17. A vesicle produced by the method for producing a vesicle according to claim 12.

* * * * *